United States Patent [19]

Randklev

[11] Patent Number: 4,966,465
[45] Date of Patent: Oct. 30, 1990

[54] METHOD FOR STORING, MIXING AND DISPENSING DENTAL MATERIALS

[75] Inventor: Ronald M. Randklev, St. Paul, Minn.

[73] Assignee: Minnesota Mining and Manufacturing Company, St. Paul, Minn.

[21] Appl. No.: 266,410

[22] Filed: Nov. 2, 1988

[51] Int. Cl.$^5$ .................... B01F 3/12; B01F 11/00; B65D 25/08

[52] U.S. Cl. .................. 366/111; 206/63.5; 206/219; 366/114; 366/130; 366/348; 366/602

[58] Field of Search ............ 366/108, 111, 130, 114, 366/241, 348, 349, 602; 206/219, 220, 222, 63.5; 215/DIG. 8

[56] References Cited

U.S. PATENT DOCUMENTS

| | | |
|---|---|---|
| 1,174,258 | 8/1930 | English . |
| 2,382,978 | 8/1945 | Curry . |
| 2,527,992 | 10/1950 | Greenberg . |
| 3,336,669 | 8/1967 | Kramer . |
| 3,337,039 | 8/1967 | Knittel et al. . |
| 3,415,361 | 12/1968 | Adams, Jr. et al. . |
| 3,476,181 | 11/1969 | Strauss et al. ............... 366/602 X |
| 3,651,932 | 3/1972 | Muhlbauer ............... 206/63.5 |
| 4,358,028 | 11/1982 | Chiquiar-Arias . |
| 4,432,768 | 2/1984 | Brown et al. . |
| 4,450,958 | 5/1984 | Prasad ........................ 206/63.5 |
| 4,526,472 | 7/1985 | Zaltsman .................... 366/602 |
| 4,542,823 | 9/1985 | Frick ........................... 366/602 |
| 4,664,257 | 5/1987 | Nilson ........................ 206/219 |
| 4,863,017 | 9/1989 | Vlock ......................... 206/219 |
| 4,871,261 | 10/1989 | Randklev ................... 366/602 |

FOREIGN PATENT DOCUMENTS

| | | | |
|---|---|---|---|
| 2012244 | 3/1970 | Fed. Rep. of Germany ...... 366/602 |
| 2027599 | 2/1980 | United Kingdom ................ 366/602 |

Primary Examiner—Timothy F. Simone
Attorney, Agent, or Firm—Donald M. Sell; Walter N. Kirn; James D. Christoff

[57] ABSTRACT

A flexible, disposable ampule is pre-dosed with a first ingredient, and a second ingredient is introduced into the ampule immediately before a mixing operation. The ampule conveniently fits within a rigid capsule adapted for use with a dental amalgamator which, when activated, thoroughly mixes the ingredients within the ampule. After the ingredients are mixed and the preparation is formed, the ampule is removed from the capsule and the preparation is dispensed by establishing an outlet opening and compressing the ampule between the distal phalange segments of a thumb and a finger.

8 Claims, 1 Drawing Sheet

METHOD FOR STORING, MIXING AND DISPENSING DENTAL MATERIALS

BACKGROUND OF THE INVENTION

1. Field of the Invention

This invention relates to a method for storing, mixing and dispensing dental materials by use of a disposable, pre-dosed, flexible ampule.

2. Description of the Related Art

The mixing of dental materials such as cements, liners and the like which include two or more ingredients is typically carried out by placing a measured quantity of each ingredient atop a mixing pad and then using a spatula to mix the ingredients and form the desired preparation. Dental materials have also been mixed in the past by placing measured quantities of each ingredient directly into a rigid capsule adapted for use with a dental amalgamator that is operable to shake the capsule and thereby mix the ingredients. In either of these circumstances, however, each ingredient of the preparation must be carefully measured and delivered to the mixing site.

Certain types of storage and mixing containers in the art include containers having two initially separate compartments which are intended to each hold one ingredient of the desired, final preparation. In such containers, the ingredients are brought into combination with one another after a seal between the compartments has been ruptured. This type of construction, however, is somewhat difficult to manufacture and also presents a risk of premature mixing due to unintentional rupture of the seal between the compartments. Moreover, these containers do not permit the end user to easily vary the proportion of the ingredients.

SUMMARY OF THE INVENTION

The present invention is directed toward a method for storing, mixing and dispensing a preparation which includes the step of providing an ampule having a closed internal chamber which is pre-dosed with a measured quantity of a first component, wherein the ampule has an overall configuration of dimensions sufficiently small such that opposite sides of the ampule are substantially covered when grasped between distal phalange segments of a thumb and a finger. The method also includes the steps of opening an aperture in a wall of the ampule to provide access to the pre-dosed chamber, introducing a second component through the aperture and into the chamber, and closing the aperture. The ampule is then oscillated to mix the first component and the second component within the chamber to form a preparation. Thereafter, an outlet opening is established in the wall of the ampule. Finally, the method includes the steps of substantially covering opposite sides of the ampule by grasping the ampule between the distal phalange segments of a thumb and a finger, and compressing the ampule between the thumb and finger to expel the preparation through the outlet opening.

Advantageously, the proportion of ingredients in the resultant preparation can be varied as desired by the user during addition of the second ingredient. Moreover, the ampule may be made of inexpensive materials and disposed of after a single use. Preferably, the outlet opening is surrounded by a neck which couples in snap-fit relation to a delivery tube so that the preparation can be dispensed directly to an application site.

DESCRIPTION OF THE PREFERRED EMBODIMENT

Figure 1:
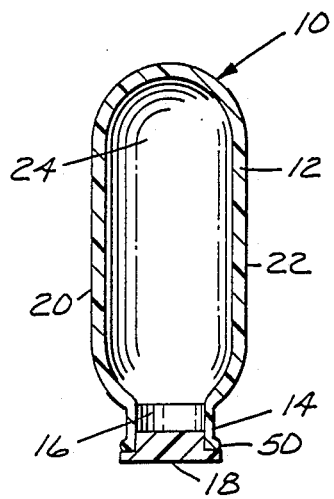
FIG. 1 is a side cross-sectional view of a storage, mixing and dispensing ampule for carrying out the method of the present invention.

A storing, mixing and dispensing ampule 10 is illustrated in FIG. 1 and has a unitary, flexible wall 12 that defines a generally oval-shaped configuration in longitudinal section and a circular configuration in transverse section. One end of the ampule 10 tapers to a somewhat cylindrical, protruding neck 14 that defines an outlet aperture or opening 16 which is initially closed by a friction-fit stopper 18.

The ampule 10 has an overall configuration of dimensions sufficiently small such that opposite sides 20, 22 of the ampule 10 are substantially covered when grasped between the distal phalange segments of a thumb and a finger. Specifically, the overall length of the ampule 10 is less than about 1.5 inches (3.8 cm.) and preferably equal to or less than about 1.31 inches (3.3 cm.), so that the entire extent of the sides 20, 22 may be grasped and compressed between the ventral sides of the tip segments of a human adult finger and thumb which are distal to the respective distal interphalangeal joint. In practice, good results have been observed by use of an ampule similar to ampule 10 having an internal chamber volume of up to about 2.5 cc. with a length to diameter ratio ranging from about 2.5/1.0 to about 3.0/1.0.

The ampule 10 has an internal chamber 24 which is pre-dosed with a single, first ingredient or component at the time of manufacture and before the ampule 10 reaches the end user. A second ingredient or component is added by the end user immediately before a mixing operation and in a quantity suitable for providing the desired proportion of the ingredients in the resultant preparation.

The second ingredient may be added to the chamber 24 by a syringe or dropper after removal of the stopper 18 to open the outlet aperture 16. Alternatively, the stopper 18 may be of a construction suitable for enabling a syringe needle to protrude through the stopper 18 and directly into the chamber 24 for addition of other ingredients.

The disposable ampule 10 may be made of any one of a number of flexible materials such as polyethylene, polypropylene or a material sold under the trademark "Surlyn" and available from DuPont. In this regard, it is important that the ingredients in the chamber 24, which may include materials such as fluoroaluminosilicate glass, polyacrylic acid, light curable resin, zinc oxide or polycarboxylate cement, do not react with the material forming the ampule 10.

Figure 3:
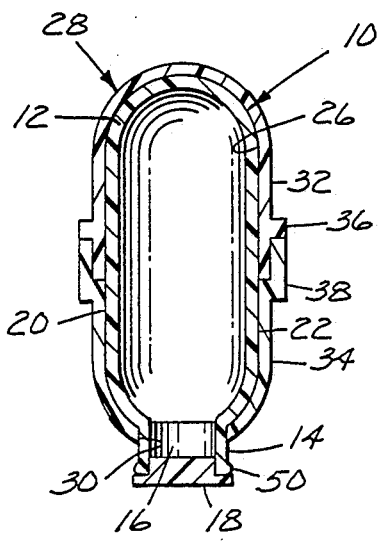
FIG. 3 is a side cross-sectional view of the ampule of FIG. 1 along with a surrounding capsule that is adapted to be used with a conventional dental amalgamator for mixing ingredients within the ampule.

Once the second ingredient has been introduced into the chamber 24, the stopper 18 is replaced in the neck 14 to close the aperture 16, and the ampule 10 is placed in a compartment 26 of a rigid capsule 28 as illustrated in FIG. 3. The compartment 26 has an oval-shaped configuration that is complemental in configuration to the normal external shape of the ampule 10, with the neck 14 of the ampule 10 protruding through a circular opening 30 formed in one end of the capsule 28.

The capsule 28 also includes a first rigid capsule segment 32 and a second rigid capsule segment 34, each of which is formed with an enlarged, circumscribing flange portion 36, 38 respectively. The flange portions 36, 38 are constructed to receive each other in sliding, telescopic relation and present a slight frictional or interference fit to retain the segments 32, 34 together. When desired, however, the flange portions 36, 38 may be readily separated by hand to insert or remove the ampule 10 from the capsule compartment 26.

The overall configuration of the capsule 28 is adapted to complementally fit within the jaws of the holding mechanism of a conventional dental amalgamator. Consequently, once the ampule 10 has been placed within the compartment 26, the capsule 28 may be placed in the jaws of the amalgamator and the amalgamator subsequently activated to reciprocate the capsule 28 and mix the components within the ampule 10.

The rigid wall of the capsule 28 functions to minimize damage to the flexible wall portions 12 of the ampule 10 during the mixing operation. Preferably, the ampule 10 is snugly received in the compartment 26 so that the ampule 10 cannot shift in a longitudinal or lateral direction relative to the capsule 28.

Next, the capsule 28 is opened by separating the flange portions 36, 38 and the ampule 10 removed from the compartment 26. An outlet opening is then established in the wall 12 of the ampule 10 by removing the stopper 18 and re-opening the aperture 16.

Figure 2:
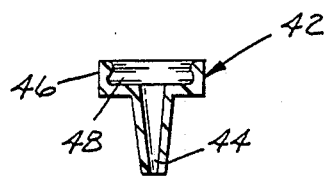
FIG. 2 is a side cross-sectional view of a delivery tube adapted for releasable connection with the ampule of FIG. 1 for delivering a mixed preparation directly to an application site.

If desired, the preparation formed from the two components mixed within the chamber 24 may be dispensed directly to an application site, optionally by use of a delivery tube 42 that is depicted in FIG. 2. The delivery tube 42 includes an internal passageway 44, and a cap region 46 that is formed with an internal, circular recess 48. The delivery tube 42 is connected to the ampule 10 in snap-fit relation and is held in place by means of an out-turned, circumscribing lip 50 that is formed on the outer end of the neck 14 of the ampule 10 as illustrated in FIG. 1.

To dispense the mixed preparation, the ampule 10 is grasped between the ventral sides of distal phalange segments of a thumb and a finger in order to substantially cover each of the sides 20, 22 of the ampule 10. Thereafter, the ampule 10 is compressed by manual pressure between the thumb and the finger to expel the mixed preparation through the outlet aperture 16. Substantially all of the contents of the ampule 10 are expelled from the chamber 24 as the flexible wall 12 is flattened to bring the ampule sides 20, 22 in substantially complete contact with each other.

Alternatively, the method may be carried out by use of an ampule having an integral, protruding neck which is formed with an integral cover. To establish the outlet aperture, a portion of the neck including the cover is severed by a knife from the remaining portions of the neck and the ampule. The opening may later be closed by use of a stopper or cap.

I claim:

1. A method for storing, mixing and dispensing a preparation comprising the steps of:
   providing an ampule having a closed internal chamber pre-dosed with a measured quantity of a first component,
   said ampule having an overall configuration of dimensions sufficiently small such that opposite sides of said ampule are substantially covered when grasped between the distal phalange segments of a user's thumb and finger;
   opening an aperture in a wall of said ampule to provide access to said chamber;
   introducing a second component through said aperture and into said chamber;
   closing said aperture;
   oscillating said ampule to mix said first component and said second component within said chamber and form a preparation;
   establishing an outlet opening in said wall of said ampule;
   substantially covering opposite sides of said ampule by grasping the ampule between the distal phalange segments of a user's thumb and finger; and
   compressing said ampule between said thumb and said finger to expel preparation through said outlet opening.

2. The method of claim 1, wherein said step of establishing said outlet opening is carried out by re-opening said aperture.

3. The method of claim 1, wherein said step of closing said aperture includes the step of placing a cap over said aperture.

4. The method of claim 1, wherein said step of closing said aperture is carried out by using a stopper.

5. The method of claim 1, wherein said step of oscillating said ampule includes the step of carrying said ampule within a substantially surrounding, rigid capsule.

6. The method of claim 5, wherein said step of oscillating said ampule is carried out by a dental amalgamator.

7. The method of claim 1, wherein said step of providing said ampule is carried out with an ampule of a size less than about 1.5 inches (3.8 cm.).

8. The method of claim 1, wherein said step of opening said aperture includes the step of severing a portion of an integral, protruding, closed neck of said ampule from remaining portions of said neck and of said ampule.

* * * * *